United States Patent
Cha

Patent Number: 5,451,302
Date of Patent: Sep. 19, 1995

[54] PROCESS FOR MICROWAVE CATALYSIS OF CHEMICAL REACTIONS USING WAVEGUIDE LIQUID FILMS

[76] Inventor: Chang Y. Cha, 3807 Reynolds St., Laramie, Wyo. 82070

[21] Appl. No.: 237,480

[22] Filed: May 3, 1994

[51] Int. Cl.$^6$ ............................................. C07B 63/00
[52] U.S. Cl. ............................ 204/157.15; 204/157.43; 204/158.2
[58] Field of Search ............ 204/157.43, 158.2, 157.15, 204/168; 423/321.1

[56] References Cited

U.S. PATENT DOCUMENTS

| | | | |
|---|---|---|---|
| 4,076,606 | 2/1978 | Suzuki et al. | 204/157.1 R |
| 4,345,983 | 8/1982 | Wan | 204/158 |
| 4,545,879 | 10/1985 | Wan et al. | 204/158 R |
| 4,671,951 | 6/1987 | Masse | 204/157.43 |
| 4,671,952 | 6/1987 | Masse | 204/157.43 |
| 5,131,993 | 7/1992 | Suib et al. | 204/168 |

OTHER PUBLICATIONS

Kirk–Othmer, Encyclopedia of Chemical Technology, Supp., 599–608, Wiley, 1981. "Plasma Technology". no month indicated.

Kirk–Othmer, Encyclopedia of Chemical Technology, 15, 494–522, Wiley, 1981. "Microwave Technology". no month indicated.

*Primary Examiner*—John Niebling
*Assistant Examiner*—C. Delacroix-Muirheid
*Attorney, Agent, or Firm*—John O. Mingle

[57] ABSTRACT

The invention utilizes microwave catalysis to catalyze desirable liquid chemical reactions between constituents flowing as a thin film within a microwave energy waveguide. Chemical reactions enhanced by this process include the concentration of phosphoric acid by removal of bound water and the release of carbon dioxide from pregnant solutions of monoethanolamine.

6 Claims, 1 Drawing Sheet

PROCESS FOR MICROWAVE CATALYSIS OF CHEMICAL REACTIONS USING WAVEGUIDE LIQUID FILMS

BACKGROUND OF INVENTION

1. Field of Invention

The present invention relates to a process using radiofrequency microwave energy to catalyze chemical reactions within a liquid film internal to the waveguide transmitting said energy.

2. Background

A liquid medium is a common place for chemical reactions since said liquid can represent a solution or mixture. Water solubility of inorganic chemicals is particularly common; however, the liquid medium is not restricted to water. When such chemical liquids are organic in nature, reactions between the liquid mixture constituents often occur slowly; thus, enhancement of such chemical reaction rates is often desirable. The subject invention positions this liquid as a thin film within an operating radiofrequency energy waveguide. The microwave energy thus catalyzes the desired chemical reactions.

Quantum radiofrequency (RF) physics is based upon the phenomenon of resonant interaction with matter of electromagnetic radiation in the microwave and RF regions since every atom or molecule can absorb, and thus radiate, electromagnetic waves of various wavelengths. The rotational and vibrational frequencies of the electrons represent the most important frequency range. The electromagnetic frequency spectrum is conveniently divided into ultrasonic, microwave, and optical regions. The microwave region runs from 300 Mhz (megahertz) to 300 Ghz (gigahertz) and encompasses frequencies used for much communication equipment. For additional information refer to N. Cook, *Microwave Principles and Systems,* Prentice-Hall, 1986.

Often the term microwaves or microwave energy is applied to a broad range of radiofrequency energies particularly with respect to the common heating frequencies, 915 MHz and 2450 MHz. The former is often employed in industrial nearing applications while the latter is the frequency of the common household microwave oven and therefore represents a good frequency to excite water molecules, in this writing the term 'microwaves' is generally employed to represent 'radiofrequency energies selected from the range of about 915 to 5000 MHz', since in a practical sense this total range is employable for the subdue invention.

The absorption of microwaves by the energy bands, particularly the vibrational energy levels, of the atoms or molecules results in the thermal activation of the nonplasma material and the excitation of valence electrons. The nonplasma nature of these interactions is important for a separate and distinct form of heating employs plasma formed by arc conditions of a high temperature, often more than 3000° F., and at much reduced pressures or vacuum conditions. For instance, refer to Kirk-Othmer, *Encyclopedia of Chemical Technology,* 3rd Edition, Supplementary Volume, pages 599–608, Plasma Technology. In microwave technology, as applied in the subject invention, neither condition is present and therefore no plasmas are formed.

These microwaves lower the effective activation energy required for desirable chemical reactions since they can act locally on a microscopic scale by exciting electrons of a specific atom in contrast to normal global heating by raising the bulk temperature. Further this microscopic interaction is favored by polar molecules whose electrons become locally excited leading to high chemical activity; however, nonpolar molecules adjacent to such polar molecules are affected to a much lesser extent. An example is the heating of polar water molecules in a common household microwave oven where the container is of nonpolar material that is microwave-passing and stays relatively cool.

A polar material interacts with microwaves readily and rapidly degrades its effective penetrating power. This aspect is employed in waveguides for microwave transmission since the waveguide transmits the energy along the skin of the guide; therefore, the guide is hollow. Such a hollow waveguide, often called a waveguide cavity, contains a substantially uniform energy field that is utilized in the subject invention to interact with a liquid film. This film of liquid if of a polar nature, like water, will quickly degrade the microwave energy and is referred to as microwave-absorbing; thus, only a thin surface layer is effective. The concept of penetration depth Is often employed to indicate the distance into a medium that is penetrated by a given frequency of radiofrequency energy. For water using 2450 MHz microwaves this penetration depth is approximately one to two centimeters.

It is common to refer to a thin film, or if appropriate thin liquid film, for such microwaves interaction. In microwave catalysis the best results occur when the polar molecules of the thin film represent a chemical reactant.

When the thin liquid film is potentially nonpolar, such as a symmetric organic molecule, and thus largely microwave-passing, most local microwaves interaction occurs with polar constituents dissolved or carried by said film. Thus first order chemical reactions, such as chemical decompositions, are the easiest to microwave catalyze.

As used above microwaves are often referred to as a form of catalysis when applied to chemical reaction rates. See Kirk-Othmer, *Encyclopedia of Chemical Technology,* 3rd Edition, Volume 15, pages 494–517, Microwave Technology.

Related U.S. patents using microwaves include:

| U.S. Pat. No. | Inventor | Year |
| --- | --- | --- |
| 4,076,606 | Suzuki et al. | 1978 |
| 4,345,983 | Wan | 1982 |
| 4,545,879 | Wan et al | 1985 |

Referring to the above list, Suzuki discloses a process for homogeneously decomposing nitrogen dioxide using microwave irradiation at the standard microwave frequency in an exhaust gas stream. Wan discloses a method for decomposing solid chlorinated hydrocarbons with a ferromagnetic catalyst using microwave heating. Wan et al disclose employing microwave heating to desulphurize pulverized petroleum pitch using a ferromagnetic catalyst.

SUMMARY OF INVENTION

The objectives of the present invention include overcoming the above-mentioned deficiencies in the prior art and providing a process for liquid film microwave catalysis.

The subject invention utilizes microwaves to enhance desirable liquid chemical reactions between constituents flowing as a thin film within a microwave energy waveguide. Chemical reactions enhanced by this process include the concentration of phosphoric acid and the release of carbon dioxide from pregnant solutions of monoethanolamine.

DETAILED DESCRIPTION OF INVENTION

Figure 1:
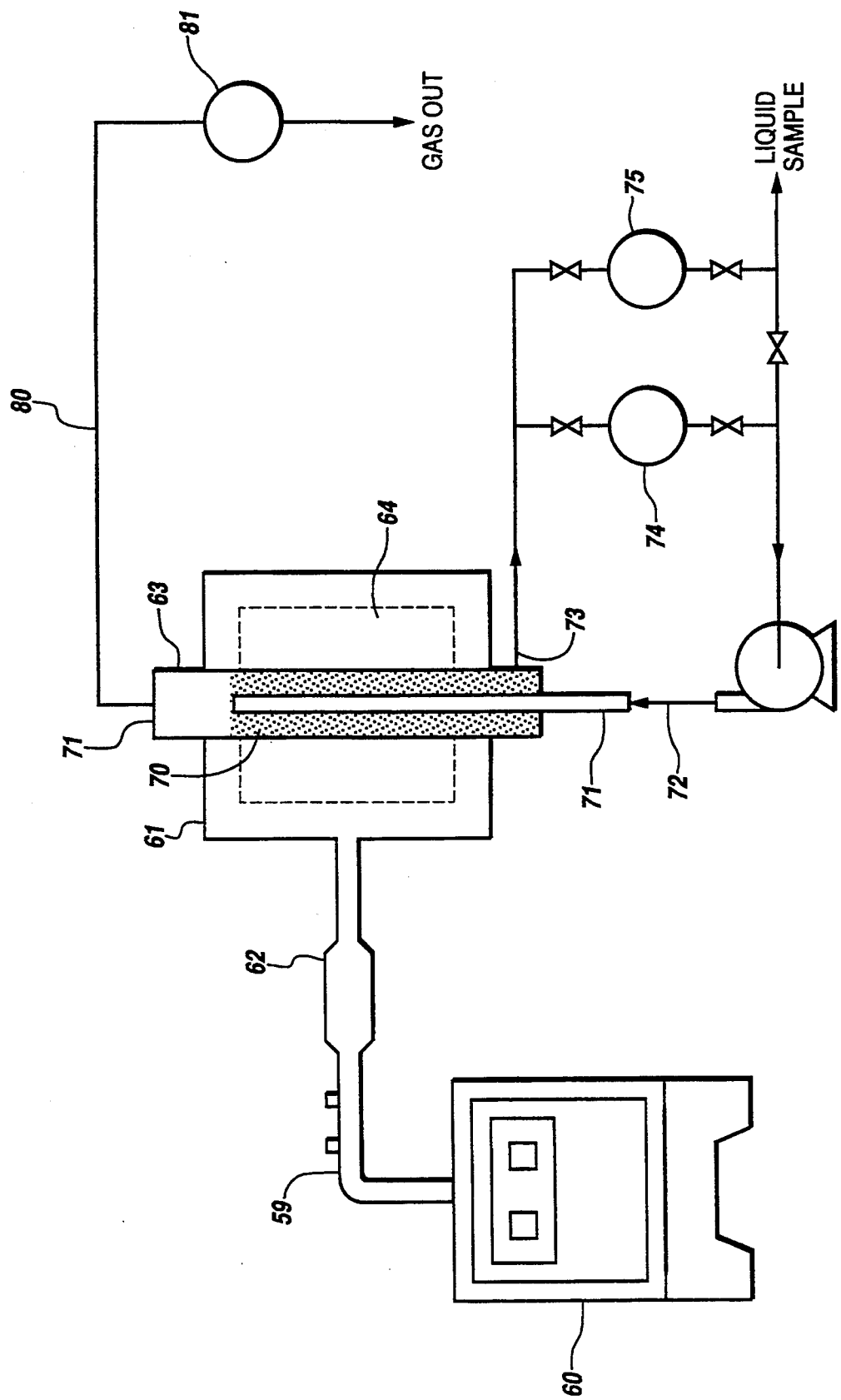
FIG. 1 shows a typical laboratory RF reactor system with a waveguide cavity creeping flow packed bed.

Microwaves are a versatile form of energy that is applicable to enhance chemical reactions since the energy is locally applied by its vibrational absorption by polar molecules and does not produce plasma conditions. Particularly reactions that proceed by free-radical mechanisms are often enhanced to higher rates because their initial equilibrium thermodynamics is unfavorable. A second class of enhanced reactions are those whose reaction kinetics appear unfavorable at desirable bulk temperature conditions.

The continuous thin film of liquid necessary to perform this microwave catalysis is generated within the waveguide by a number of means. One method ms to create creeping flow down a tube, either inside or outside, by employing a flow guide at the top end of the tube. Since this occurs in the microwave field, these components, such as quartz tubes, are microwave-passing in nature. The residence time of the liquid in the microwave energy field governs the microwave catalytic effect and is increased by having a longer waveguide and longer quartz tubes. Alternatively by increasing the microwave generator power level a shorter residence time is employable. For larger flow regimes a series of plates positioned within the waveguide cavity allows a greater surface for required flow of the thin liquid film.

Another method of creating a thin film of liquid is to utilize creeping flow through a packed bed. The packing material, such as glass beads, is microwave-passing so that the microwave catalysis occurs substantially within the thin film of liquid flowing over said packing.

Therefore either the surface or substrate of a microwave-passing tube, plate, packed bed, or combinations thereof, with creeping thin film liquid flow over it is employable.

Thus equivalents for a thin flow of liquid film include the flow regimes of sheet, creeping, moving bed, packed bed, and combinations thereof. However a static batch system placed within the waveguide cavity is not an equivalent since the small penetration depth of the microwaves only catalyzes a thin outside region; therefore, an equivalent batch system must be well stirred at all times.

A typical laboratory microwave reactor system to study experimental conditions for liquid film microwave catalysis is shown in FIG. 1. A standard commercial microwave energy generator 60 was utilized that was coupled 59 with microwave transmitting waveguide 61 through a frequency tuner 62 to the microwave chemical reactor 63. The reactor 63 was internal to the waveguide 61 and was positioned in the waveguide cavity 64. As shown the reactor was a packed bed 70, in this instance glass beads, situated between concentric quartz tubes 71. The flow liquid was pumped 72 slowly up through the center tube and overflowed running down through the packed bed 70 in creeping, film flow. The liquid left 73 the bottom of the packed bed 70 and was collected 74 and sampled 75. The liquid samples were analyzed at convenient times. The overhead gas 80 was metered 81 before release. Alternatively said gas was also analyzed, such as with a gas chromatograph. Further, sometimes a sweep gas, such as nitrogen, was employed to enhance any gaseous reaction prodtact disengagement.

In use the microwave energy 60 was adjusted in power to produce good measurable results for the concentrations selected. It was likely microwave tuned 62 to the particular laboratory reaction chamber utilized in this small setup; however, in commercial sized units tuning 62 was unnecessary as the larger size of the reaction chamber reflected the microwaves until absorbed within the reactor 63. As shown the reacting liquid was recirculated several times through the reactor.

Alternatively the reactor was creeping flow between two concentric quartz tubes where the distance between the tubes was small enough and the flow so adjusted to allow creeping flow alternating between the outside of the inner tube and the inside of the outer tube. A further alternative was to utilize a single tube with an appropriate flow distributor to allow creeping flow down the inner wall of said tube.

The microwave energy field interacted substantially with polar constituents of the liquid mixture. Said polar constituent's were microwave-absorbing; in contrast the quartz tubes and other materials employed were microwave-passing and interacted very little with said field. The liquid itself could be polar, such as water, or the molecules carried by the liquid could be polar, or both. If appropriate energy was absorbed by such reactant polar molecules, microwave catalysis occurred causing reaction products to be formed. If such products were gases they escaped the liquid and flowed out of the reactor. Alternatively some products could be polar themselves, like water, and thus be vaporized to gases by the microwave energy field.

In all instances an important aspect of the process of the subject invention was that the chemical reactor was situated in the waveguide cavity as shown in FIG. 1. This insured a substantially uniform radiofrequency energy field of known power to perform microwave catalysis. Conversely if a conventional microwave oven is employed no waveguide is present since the generator directs the energy into the oven in a nonuniform field pattern and produces inconsistent results. Because of the thin penetration depth in the liquid for these microwaves, the consistency of the radiofrequency field in the waveguide cavity is needed to perform this microwave catalysis in liquid mediums. However much prior art utilized such an inferior microwave oven setup.

As a first example carbon dioxide was decomposed from saturated or pregnant monoethanolamine, commonly abbreviated as MEA. The expected reactions were:

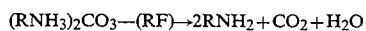

$(RNH_3)_2CO_3 —(RF)\rightarrow 2RNH_2 + CO_2 + H_2O$

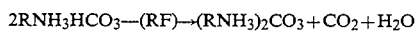

$2RNH_3HCO_3 —(RF)\rightarrow (RNH_3)_2CO_3 + CO_2 + H_2O$

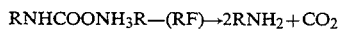

$RNHCOONH_3R —(RF)\rightarrow 2RNH_2 + CO_2$ where R was $HO-CH_2-CH_2-$ and MEA was $RNH_2$. Here "—(RF)→" means the reaction was catalyzed in the direction indicated by radiofrequency energy in the microwave range. The carbon dioxide gas disengaged from the liquid film flows away and was vented or recovered. Such $CO_2$ flow was potentially enhanced by using a bleed gas such as nitrogen.

To obtain the $CO_2$ saturated MEA solution one kilogram of 15% MEA solution was bubbled with pure carbon dioxide for 15 hours. After regeneration with microwave catalysis, the solution was subject to resaturation with $CO_2$. The microwave generator power at 2450 MHz was in the range of 400–800 watts with the bulk temperature maintained below about 200° F. The waveguide cavity was sized at 17.71×17.71×19.68, all in inches. Table 1 gave the results of four tests. Tests one and two were performed with creeping flow between inner and outer quartz tubes, 0.25 inch and 1.75 inch respectively. Tests three and four were performed using a packed bed of ⅛ inch glass beads and repeated flow cycles. Test number four was performed with resaturated solution from the third test and with a nitrogen sweep gas.

In the best mode 97 percent of the carbon dioxide in the saturated MEA was released; however, in most instances more than about 50 percent release was obtained. In all cases reabsorption capacity was excellent at above 90 percent.

In a further example phosphoric acid solution was concentrated by the removal of bound water. In particular the bound water was microwave catalyzed into being released or disengaged from the phosphoric acid and was then vaporized for flow removal. The experimental arrangement was similar to the above case except that a ¾ inch diameter quartz tube was centered in the waveguide cavity and creeping thin film flow of the phosphoric acid solution was utilized down the inner wall of said quartz tube. The microwave generator power of 400–500 watts was employed. The feed amount of dilute phosphoric acid was 767 grams and 241 grams of water were collected from the overhead gas by a condenser. The product amount of 526 grams was a very thick concentrated phosphoric acid. In addition at these operating conditions some solid phosphoric acid was deposited in the quartz tube. Operating in the best mode the flow rate along

TABLE 1

| Monoethanolamine Data for Carbon Dioxide Removal | | | | |
|---|---|---|---|---|
| Run Number | 1 | 2 | 3 | 4 |
| $CO_2$ Conc., mole $CO_2$/mole MEA | | | | |
| Saturated Solution | 0.71 | 0.68 | 0.68 | 0.64 |
| Regenerated Solution | 0.39 | 0.26 | 0.19 | 0.02 |
| Resaturated Solution | 0.68 | 0.64 | 0.62 | — |
| $CO_2$ Released, % of $CO_2$ in | 45 | 62 | 72 | 97 |
| Solution Reabsorption Capacity, % of $CO_2$ Released | 96 | 94 | 91 | — | with the microwave power level is adjustable to concentrate the phosphoric acid without any solid formation.

Microwave catalysis of other desirable chemical reactions carried out in a liquid state can be performed by variations of the above expressed examples employing equivalents.

The foregoing description of the specific embodiments will so fully reveal the general nature of the invention that others can, by applying current knowledge, readily modify and/or adapt for various applications such specific embodiments without departing from the generic concept, and therefore such adaptations or modifications are intended to be comprehended within the meaning and range of equivalents of the disclosed embodiments. It is to be understood that the phraseology or terminology herein is for the purpose of description and not of limitation.

I claim:

1. A method for carbon dioxide saturated monoethanolamine processing comprising:
   acquiring a continuous thin liquid film of said monoethanolamine flowing upon a microwave-passing substrate;
   position said thin liquid film within a waveguide microwave energy field selected from the frequency range of about 915 to 5000 MHz; and removing gaseous carbon dioxide.

2. The method according to claim 1 wherein said continuous thin liquid film further comprises creeping flow.

3. The method according to claim 1 wherein said microwave-passing substrate further comprises selection from the group consisting of tube, plate, packed bed and combinations thereof.

4. The method according to claim 1 wherein said carbon dioxide further comprises a removal efficiency of more than fifty percent.

5. The method according to claim 1 wherein said carbon dioxide further comprises enhancement with sweep gas removal.

6. A method for microwave catalysis of chemically saturated monoethanolamine comprising:
   positioning a thin liquid film containing said monoethanolamine solution within a waveguide microwave energy field; and
   removing a gaseous reaction product as carbon dioxide.

* * * * *